United States Patent

Obata et al.

[11] Patent Number: 5,252,596
[45] Date of Patent: Oct. 12, 1993

[54] PHENOXYALKYLAMINE DERIVATIVE AND METHOD FOR CONTROLLING NOXIOUS ORGANISMS CONTAINING THE SAME

[75] Inventors: Tokio Obata; Katsutoshi Fujii; Akira Ooka; Shoji Shikita, all of Ube, Japan

[73] Assignee: UBE Industries, Ltd., Yamaguchi, Japan

[21] Appl. No.: 903,940

[22] Filed: Jun. 26, 1992

[30] Foreign Application Priority Data

Jun. 28, 1991 [JP] Japan .................................. 3-252717
Aug. 30, 1991 [JP] Japan .................................. 3-298592
Nov. 26, 1991 [JP] Japan .................................. 3-355387

[51] Int. Cl.$^5$ .................... A61K 43/56; C07D 231/54
[52] U.S. Cl. .................................. 514/403; 548/360.1
[58] Field of Search ........................ 548/369, 360.1; 514/403

[56] References Cited

U.S. PATENT DOCUMENTS 5,039,692 8/1991 Obata et al. .......................... 514/406

FOREIGN PATENT DOCUMENTS 3-153668 7/1991 Japan .

*Primary Examiner*—Robert W. Ramsuer
*Attorney, Agent, or Firm*—Finnegan, Henderson, Farabow, Garrett & Dunner

[57] ABSTRACT

Disclosed are a novel phenoxyalkylamine compound represented by the following formula:

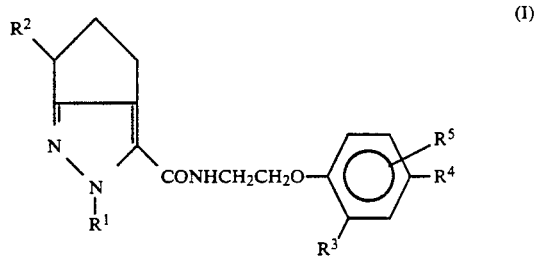

wherein $R^1$ represents a lower alkyl group or a lower haloalkyl group; $R^2$ represents hydrogen atom or a lower alkyl group; $R^3$ represents hydrogen atom, a lower alkyl group or a halogen atom; $R^4$ represents a lower alkenyl group or $-S-O-R^6$ where A represents a lower alkylene group and $R^6$ represents a lower alkyl group, a lower alkenyl group or a lower alkynyl group; $R^5$ represents hydrogen atom, a lower alkyl group or a halogen atom, a method for preparing the same and a chemical for controlling noxious organisms which contains the same as an active ingredient.

8 Claims, No Drawings

PHENOXYALKYLAMINE DERIVATIVE AND METHOD FOR CONTROLLING NOXIOUS ORGANISMS CONTAINING THE SAME

BACKGROUND OF THE INVENTION

This invention relates to a novel phenoxyalkylamine derivative which is a chemical for controlling noxious organisms useful as an insecticide, an acaricide and a fungicide.

In the prior art, there have been known a large number of phenoxyalkylamine derivatives as agricultural chemicals. For example, there have been reported quinazoline derivatives in Japanese Provisional Patent Publications No. 17123/1979, No. 76803/1980 and No. 76804/1980, a pyridopyrimidine derivative in Japanese Provisional Patent Publication No. 108806/1980, a thienopyrimidine derivative in Japanese Provisional Patent Publication No. 42387/1984, and pyrimidine derivatives in Japanese Provisional Patent Publications No. 36666/1984, No. 36667/1984, No. 286373/1986 and No. 67/1987.

However, a novel cyclopenta[1,2-c]-3-pyrazolecarboxamide derivative such as the compound of the present invention has not been reported at all.

Thus, its activity as a chemical for controlling noxious organisms useful as an insecticide, an acaricide and a fungicide has not been known.

SUMMARY OF THE INVENTION

An object of the present invention is to provide a novel phenoxyalkylamine derivative, a method for preparing the same and a chemical for controlling noxious organisms useful as an insecticide, an acaricide and a fungicide which contains said derivative as an active ingredient.

The present inventors have studied intensively in order to solve the above task, and consequently found that a novel phenoxyalkylamine derivative has remarkable controlling activity as a chemical for controlling noxious organisms useful as an insecticide, an acaricide and a fungicide, to accomplish the present invention.

That is, a first invention is concerned to a phenoxyalkylamine derivative represented by the following formula:

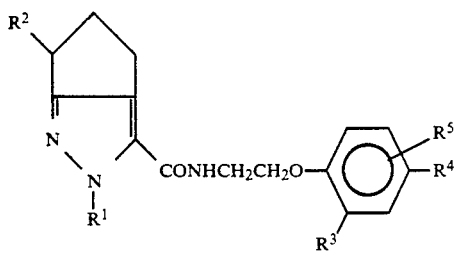

wherein
$R^1$ represents a lower alkyl group or a lower haloalkyl group; $R^2$ represents hydrogen atom or a lower alkyl group; $R^3$ represents hydrogen atom, a lower alkyl group or a halogen atom; $R^4$ represents a lower alkenyl group or —A—O—$R^6$ where A represents a lower alkylene group and $R^6$ represents a lower alkyl group, a lower alkenyl group or a lower alkynyl group;

$R^5$ represents hydrogen atom, a lower alkyl group or a halogen atom.

A second invention is concerned to a method for preparing the phenoxyalkylamine derivative represented by the above formula (I), which comprises reacting a cyclopenta[1,2-c]-3-pyrazolecarboxylic acid derivative represented by the following formula:

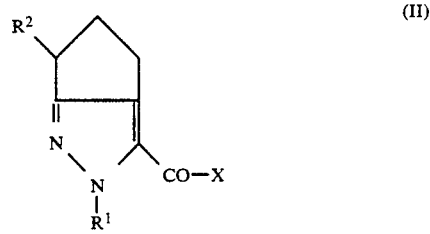

wherein
$R^1$ and $R^2$ each have the same meanings as defined above; and X represents a halogen atom
with a phenoxyalkylamine represented by the following formula:

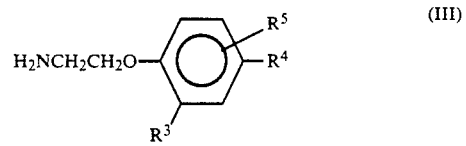

wherein $R^3$, $R^4$ and $R^5$ each have the same meanings as defined above.

A third invention is concerned to an insecticide, an acaricide and a fungicide which contain the phenoxyalkylamine derivative represented by the above formula (I) as an active ingredient.

DESCRIPTION OF THE PREFERRED EMBODIMENTS

In the following, the present invention is explained in detail.

In the above novel phenoxyalkylamine derivative (I) which is the desired compound, and the cyclopenta[1,2-c]-3-pyrazolecarboxylic acid derivative (II) and the phenoxyalkylamines (III) which are starting materials thereof, $R^1$, $R^2$, $R^3$, $R^4$, $R^5$, $R^6$ and X are as described below.

As $R^1$, there may be mentioned a straight or branched lower alkyl group having 1 to 4 carbon atoms (e.g. methyl group, ethyl group, n-propyl group, i-propyl group, n-butyl, group, i-butyl group and t-butyl group), and a straight or branched lower haloalkyl group having 1 to 4 carbon atoms (e.g. trifluoromethyl group, difluoromethyl group, 2-fluoroethyl group, 2-chloroethyl group, 2,2,2-trifluoroethyl group and 3,3,3-trifluoropropyl group). The lower alkyl group is preferably methyl group, and the lower haloalkyl group is preferably 2,2,2-trifluoroethyl group.

As $R^2$, there may be mentioned hydrogen atom and a straight or branched lower alkyl group having 1 to 4 carbon atoms (e.g. the lower alkyl group described above as $R^1$), and preferred are hydrogen atom or methyl group.

As $R^3$, there may be mentioned hydrogen atom, a straight or branched lower alkyl group having 1 to 4 carbon atoms (e.g. the lower alkyl group described above as $R^1$), a halogen atom (e.g. chlorine atom, iodine atom, bromine atom and fluorine atom), and preferred is methyl group.

As R⁴, there may be mentioned a straight or branched lower alkenyl group having 3 to 5 carbon atoms (e.g. allyl group, 1-butenyl group, 2-butenyl group, 1-methylallyl group, 2-methylallyl group, 2-pentenyl group and isoprenyl group), and —A—O—R⁶ (A represents a straight or branched lower alkylene group having 1 to 4 carbon atoms (e.g. methylene group, ethylene group, propylene group and butylene group); and R⁶ represents a straight or branched lower alkyl group having 1 to 4 carbon atoms (e.g. the lower alkyl group described above as R¹), a straight or branched lower alkenyl group having 3 to 5 carbon atoms (e.g. allyl group, 1-butenyl group, 2-butenyl group, 1-methylallyl group, 2-methylallyl group, 2-pentenyl group and isoprenyl group), or a straight or branched lower alkynyl group having 3 to 4 carbon atoms (e.g. 1-propynyl group, 2-propynyl group and 2-butynyl group). Preferred are allyl group, ethoxymethyl group, 2-methoxyethyl group, 2-ethoxyethyl group, 2-propoxyethyl group, 2-butoxyethyl group, 2-allyloxyethyl group and 2-propargyloxyethyl group.

As $R^5$, there may be mentioned hydrogen atom, a straight or branched lower alkyl group having 1 to 4 carbon atoms (e.g. the lower alkyl group described above as $R^1$) and a halogen atom (e.g. chlorine atom, iodine atom, bromine atom and fluorine atom), and preferred is methyl group. When $R^5$ is not hydrogen atom, a substitution position is preferably 3-position or 6-position.

X is a halogen atom (e.g. chlorine atom, iodine atom, bromine atom and fluorine atom).

Specific examples of the compound (I) of the present invention are shown in Tables 1 to 4.

TABLE 1

| Compound No. | $R^1$ | $R^2$ | $R^3$ | $R^4$ | $R^5$ | Physical property |
|---|---|---|---|---|---|---|
| 1 | CH₃ | H | CH₃ | —CH₂CH=CH₂ | H | m.p. 77~79° C. |
| 2 | " | " | " | —CH₂CH₂OCH₃ | " | m.p. 76~78° C. |
| 3 | " | " | " | —CH₂CH₂OC₂H₅ | " | m.p. 88~90° C. |
| 4 | " | " | " | —CH₂CH₂OC₃H₇-n | H | m.p. 106~108° C. |
| 5 | " | " | " | —CH₂CH₂OCH₂CH=CH₂ | " | m.p. 92~94° C. |
| 6 | " | " | " | —CH₂CH₂OCH₂C≡CH | " | m.p. 94~96° C. |
| 7 | " | " | " | —CH₂CH₂OC₂H₅ | 3-CH₃ | m.p. 95~96° C. |
| 8 | " | " | " | —CH₂CH—OCH₃<br>            \|<br>            C₂H₅ | H | m.p. 89~90° C. |

TABLE 2

| Compound No. | $R^1$ | $R^2$ | $R^3$ | $R^4$ | $R^5$ | Physical property |
|---|---|---|---|---|---|---|
| 9 | C₂H₅ | H | CH₃ | —CH₂CH₂OC₂H₅ | H | m.p. 60~62° C. |
| 10 | CH₃ | CH₃ | " | —CH₂CH₂OCH₃ | " | m.p. 64~66° C. |
| 11 | " | " | " | —CH₂CH₂OC₂H₅ | " | m.p. 80~82° C. |
| 12 | " | " | " | —CH₂CH₂OCH₂CH=CH₂ | " | m.p. 60~62° C. |
| 13 | " | " | " | —CH₂CH₂OCH₂C≡CH | " | m.p. 101~103° C. |
| 14 | " | " | " | —CH₂CH₂OC₂H₅ | 3-CH₃ | m.p. 91~93° C. |
| 15 | C₂H₅ | " | " | " | H | |
| 16 | t-C₄H₉ | " | " | " | " | |

TABLE 3

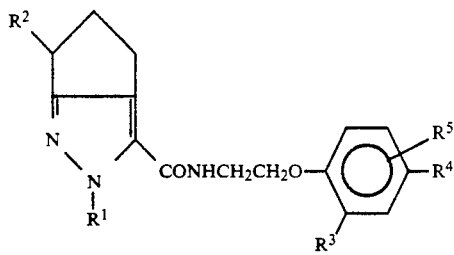

| Compound No. | R¹ | R² | R³ | R⁴ | R⁵ | Physical property |
|---|---|---|---|---|---|---|
| 17 | $CH_3$ | H | H | $-CH_2CH_2OCH_3$ | H | m.p. 83~84° C. |
| 18 | " | " | $CH_3$ | $-CH_2CH_2OC_2H_5$ | 6-$CH_3$ | |
| 19 | " | $CH_3$ | " | " | " | m.p. 102~104° C. |
| 20 | " | " | " | $-CH_2CH_2OC_3H_7$-n | H | m.p. 60~62° C. |
| 21 | t-$C_4H_9$ | H | " | $-CH_2CH_2OC_2H_5$ | " | m.p. 101~102° C. |
| 22 | $-CH_2CF_3$ | " | " | " | " | m.p. 108~109° C. |
| 23 | $CH_3$ | " | " | $-CH_2OC_2H_5$ | " | |
| 24 | " | $CH_3$ | " | " | | |

TABLE 4

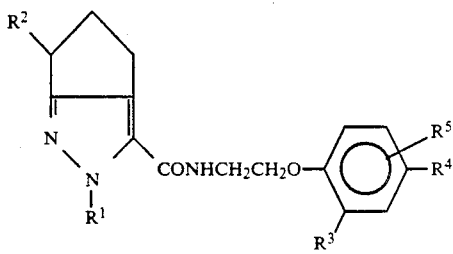

| Compound No. | R¹ | R² | R³ | R⁴ | R⁵ | Physical property |
|---|---|---|---|---|---|---|
| 25 | $CH_3$ | H | $CH_3$ | $-CH_2OC_2H_5$ | 6-$CH_3$ | |
| 26 | " | $CH_3$ | " | " | " | |
| 27 | " | H | " | $-CH_2OC_3H_7$-n | H | |
| 28 | " | $CH_3$ | " | " | 6-Cl | |
| 29 | " | H | " | $-CH_2CH_2CH_2OCH_3$ | " | |
| 30 | " | $CH_3$ | " | $-CH_2CH=CH_2$ | H | |

Among the compounds in Tables 1 to 4, preferred are Compounds 1, 2, 3, 4, 5, 7, 8, 10, 11, 12, 13, 14, 19 and 20.

The compound (I) of the present invention can be synthesized according to the following method.

The compound (I) of the present invention can be generally synthesized as shown below by reacting the starting compound (II) with the starting compound (III) in the presence or absence of a solvent, preferably in the presence of a base for accelerating the reaction.

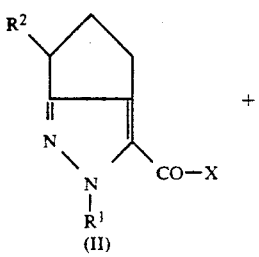

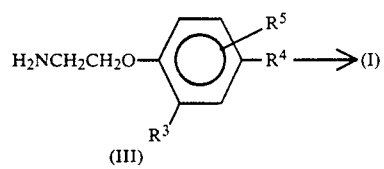

wherein R¹, R², R³, R⁴ and R⁵ each have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloromethane, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; organic bases such as triethylamine, pyridine and N,N-dimethylaniline; 1,3-dimethyl-2-imidazolidinone; dimethylsulfoxide and a mixture of the above solvents.

The solvent may be used in such an amount that the concentration of the compound (II) becomes 5 to 80 % by weight, preferably 10 to 70 % by weight.

The base is not particularly limited, and may include, for example, organic bases such as triethylamine, pyridine and N,N-dimethylaniline and 1,8-diazabicyclo[5.4.0]-7-undecene (DBU); alkali metal alkoxides such as sodium methoxide and sodium ethoxide; and inorganic bases such as sodium hydride, sodium amide, sodium hydroxide, potassium hydroxide, sodium carbonate, sodium hydrogen carbonate and potassium carbonate. Preferred are organic bases such as triethylamine, pyridine, N,N-dimethylaniline and DBU.

The amount of the base to be used may be 0.001 to 5 mole, preferably 0.8 to 1.5 mole per mole of the compound (II).

The reaction temperature is not particularly limited, but may be in the temperature range of ice cooling temperature to a boiling point or lower of a solvent used, preferably 0° C. to 10° C.

The reaction time varies depending on the above concentration and temperature, but may be generally 0.3 to 2 hours.

The amount of the compound (III) to be used is 0.5 to 2 mole, preferably 0.8 to 1.5 mole per mole of the compound (II).

The compound (II) to be used in the present invention can be prepared easily by using 2-ketocyclopentylglyoxalates and hydrazines according to, for example, a method described in Ann. Chem., 536, 97 (1938).

The compound (III) to be used in the present invention can be prepared easily according to a known method shown in the following scheme.

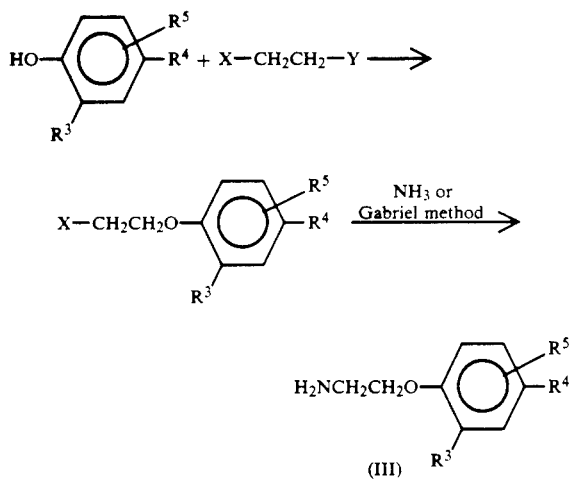

wherein $R^3$, $R^4$, $R^5$ and X each have the same meanings as defined above; and Y represents an eliminatable group.

As the eliminatable group, there may be mentioned a halogen atom such as chlorine and bromine, an alkanesulfonic acid residue and an arylsulfonic acid residue.

As the compound (III), there may be mentioned, for example, the respective compounds (III) (referred to as Compounds $(III)_1$ to $(III)_{30}$) comprising the respective kinds of substituents corresponding to Compounds No. 1 to No. 30 shown in Tables 1 to 4 (for example, Compound $(III)_1$ corresponding to Compound No. 1 means a compound wherein $R^3$ is methyl group, $R^4$ is allyl group and $R^5$ is hydrogen atom in the formula represented by the compound (III)).

After completion of the reaction, the desired compound (I) prepared as described above is subjected to common post-treatments such as extraction, concentration and filtration, and if necessary, it can be suitably purified by a conventional means such as recrystallization and various chromatographies.

As the compound (I), there may be mentioned, for example, the respective compounds (I) (referred to as Compounds 1 to 30) comprising the respective kinds of substituents corresponding to Compounds No. 1 to No. 30 shown in Tables 1 to 4 (for example, Compound 1 corresponding to Compound No. 1 means a compound wherein $R^1$ and $R^3$ are methyl groups, $R^4$ is allyl group and $R^2$ and $R^5$ are hydrogen atoms in the formula represented by the compound (I)).

As the noxious organisms on which controlling effect by the compound (I) of the present invention can be observed, there may be mentioned agricultural and horticultural noxious insects (e.g. Hemiptera (planthoppers, leafhoppers, aphides and whiteflies), Lepidoptera (cabbage armyworms, diamond-back moth, leafroller moths, pyralid moths and common cabbage worm), Coleoptera (Tenebrionid beetles, leafbeetles, weevils and scarabs) and Acarina (citrus red mite and two-spotted spider mite of Tetranychidae family and pink citrus rust mite of Eriophyidae family)), hygienically noxious insects (e.g. flies, mosquitos and cockroaches), noxious insects of stored grains (rust-red flour beetles and bean weevils), and root knot nematode, pine wood nematode and bulb mite in soil, etc., and also agricultural and horticultural diseases (e.g. brown rust (wheat), powdery mildew (barley), downy mildew (cucumber), blast (rice) and late blight (tomato)).

The phenoxyalkylamine derivative which is the chemical for controlling noxious organisms of the present invention has remarkable insecticidal, acaricidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, bentonite, clay, kaolin, diatomaceous earth, white carbon, vermiculite, calcium hydroxide, siliceous sand, ammonium sulfate and urea; a liquid carrier such as hydrocarbons (kerosine and mineral oil), aromatic hydrocarbons (benzene, toluene and xylene), chlorinated hydrocarbons (chloroform and carbon tetrachloride), ethers (dioxane and tetrahydrofuran), ketones (acetone, cyclohexanone and isophorone), esters (ethyl acetate, ethylene glycol acetate and dibutyl maleate), alcohols (methanol, n-hexanol and ethylene glycol), polar solvents (dimethylformamide and dimethylsulfoxide) and water; and a gas carrier such as air, nitrogen, carbon dioxide and freon (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignin sulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50 % by weight in an emulsion, generally 0.3 to 25 % by weight in a dust, generally 1 to 90 % by weight in a wettable powder, generally 0.5 to 5 % by weight in a granule, generally 0.5 to 5 % by weight in an oily suspension, and generally 0.1 to 5 % by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Examples, but the scope of the present invention is not limited by these Examples.

Example 1 (Syntheses of compounds (I))

(1) Synthesis of N-[2-(4-allyl-2-methylphenoxy)ethyl]-2-methyl-cyclopenta[1,2-c]-3-pyrazolecarboxamide (Compound 1)

In 1.5 ml of thionyl chloride was refluxed 0.9 g of 2-methyl-cyclopenta[1,2-c]-3-pyrazolecarboxylic acid under heating for 3 hours.

After completion of the reaction, excessive thionyl chloride was removed under reduced pressure to obtain 2-methyl-cyclopenta[1,2-c]-3-pyrazolecarboxylic acid chloride. The product obtained was dissolved in 10 ml of toluene, and the solution was added dropwise to a solution of 1.13 g of 2-(4-allyl-2-methylphenoxy)ethylamine and 0.8 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.4 g of the title compound.

(2) Synthesis of N-(2-[4-(2-methoxyethyl)-2-methyl-phenoxy]ethyl)-2-methyl-cyclopenta[1,2-c]-3-pyrazolecarboxamide (Compound 2)

In 1.5 ml of thionyl chloride was refluxed 0.9 g of 2-methyl-cyclopenta[1,2-c]-3-pyrazolecarboxylic acid under heating for 3 hours.

After completion of the reaction, excessive thionyl chloride was removed under reduced pressure to obtain 2-methyl-cyclopenta[1,2-c]-3-pyrazolecarboxylic acid chloride. The product obtained was dissolved in 10 ml of toluene, and the solution was added dropwise to a solution of 1.25 g of 2-[4-(2-methoxyethyl)-2-methyl-phenoxy]ethylamine and 0.8 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.4 g of the title compound.

(3) Synthesis of N-(2-[4-(2-ethoxyethyl)-2-methylphenoxy]ethyl}-2-methyl-cyclopenta[1,2-c]-3-pyrazolecarboxamide (Compound 3)

In 3 ml of thionyl chloride was refluxed 2.0 g of 2-methylcyclopenta[1,2-c]-3-pyrazolecarboxylic acid under heating for 3 hours.

After completion of the reaction, excessive thionyl chloride was removed under reduced pressure to obtain 2-methyl-cyclopenta[1,2-c]-3-pyrazolecarboxylic acid chloride. The product obtained was dissolved in 20 ml of toluene, and the solution was added dropwise to a solution of 3.0 g of 2-[4-(2-ethoxyethyl)-2-methyl-phenoxy]ethylamine and 1.8 g of triethylamine dissolved in 20 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 3.5 g of the title compound.

(4) Synthesis of N-(2-[4-(2-n-propoxyethyl)-2-methylphenoxy]ethyl)-2-methyl-cyclopenta[1,2-c]-3-pyrazolecarboxamide (Compound 4)

In 1.5 ml of thionyl chloride was refluxed 0.9 g of 2-methyl-cyclopenta[1,2-c]-3-pyrazolecarboxylic acid under heating for 3 hours.

After completion of the reaction, excessive thionyl chloride was removed under reduced pressure to obtain 2-methyl-cyclopenta[1,2-c]-3-pyrazolecarboxylic acid chloride. The product obtained was dissolved in 10 ml of toluene, and the solution was added dropwise to a solution of 1.41 g of 2-[4-(2-n-propoxyethyl)-2-methyl-phenoxy]-ethylamine and 0.8 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.4 g of the title compound.

(5) Synthesis of N-(2-[4-(2-allyloxyethyl)-2-methylphenoxy]ethyl)-2-methyl-cyclopenta[1,2-c]-3-pyrazolecarboxamide (Compound 5)

In 1.5 ml of thionyl chloride was refluxed 0.9 g of 2-methyl-cyclopenta[1,2-c]-3-pyrazolecarboxylic acid under heating for 3 hours.

After completion of the reaction, excessive thionyl chloride was removed under reduced pressure to obtain 2-methyl-cyclopenta[1,2-c]-3-pyrazolecarboxylic acid chloride. The product obtained was dissolved in 10 ml of toluene, and the solution was added dropwise to a solution of 1.41 g of 2-[4-(2-allyloxyethyl)-2-methyl-phenoxy]-ethylamine and 0.8 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.6 g of the title compound.

(6) Synthesis of
N-(2-[4-(2-methoxyethyl)-2-methyl-phenoxy]ethyl)-2,6-dimethyl-cyclopenta[1,2-c]-3-pyrazolecarboxamide
(Compound 10)

In 1.5 ml of thionyl chloride was refluxed 0.72 g of 2,6-dimethyl-cyclopenta[1,2-c]-3-pyrazolecarboxylic acid under heating for 3 hours.

After completion of the reaction, excessive thionyl chloride was removed under reduced pressure to obtain 2,6-dimethyl-cyclopenta[1,2-c]-3-pyrazolecarboxylic acid chloride. The product obtained was dissolved in 10 ml of toluene, and the solution was added dropwise to a solution of 0.92 g of 2-[4-(2-methoxyethyl)-2-methyl-phenoxy]-ethylamine and 0.6 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.0 g of the title compound.

(7) Synthesis of
N-{2-[4-(2-ethoxyethyl)-2-methyl-phenoxy]ethyl}-2,6-dimethyl-cyclopenta[1,2-c]-3-pyrazolecarboxamide
(Compound 11)

In 1.5 ml of thionyl chloride was refluxed 0.7 g of 2,6-dimethyl-cyclopenta[1,2-c]-3-pyrazolecarboxylic acid under heating for 3 hours.

After completion of the reaction, excessive thionyl chloride was removed under reduced pressure to obtain 2,6-dimethyl-cyclopenta[1,2-c]-3-pyrazolecarboxylic acid chloride. The product obtained was dissolved in 10 ml of toluene, and the solution was added dropwise to a solution of 0.98 g of 2-[4-(2-ethoxyethyl)-2-methyl-phenoxy]-ethylamine and 0.6 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.1 g of the title compound.

(8) Synthesis of
N-(2-[2,3-dimethyl-4-(2-ethoxyethyl)-phenoxy)ethyl)-2,6-dimethyl-cyclopenta[1,2-c]-3-pyrazolecarboxamide
(Compound 14)

In 1.5 ml of thionyl chloride was refluxed 0.7 g of 2,6-dimethyl-cyclopenta[1,2-c]-3-pyrazolecarboxylic acid under heating for 3 hours.

After completion of the reaction, excessive thionyl chloride was removed under reduced pressure to obtain 2,6-dimethyl-cyclopenta[1,2-c]-3-pyrazolecarboxylic acid chloride. The product obtained was dissolved in 10 ml of toluene, and the solution was added dropwise to a solution of 1.04 g of 2-[2,3-dimethyl-4-(2-ethoxyethyl)-phenoxy]-ethylamine and 0.6 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.2 g of the title compound.

(9) Synthesis of
N-(2-[2,6-dimethyl-4-(2-ethoxyethyl)-phenoxy]ethyl)-2,6-dimethyl-cyclopenta[1,2-c]-3-pyrazolecarboxamide
(Compound 19)

In 1.5 ml of thionyl chloride was refluxed 0.7 g of 2,6-dimethyl-cyclopenta[1,2-c]-3-pyrazolecarboxylic acid under heating for 3 hours.

After completion of the reaction, excessive thionyl chloride was removed under reduced pressure to obtain 2,6-dimethyl-cyclopenta[1,2-c]-3-pyrazolecarboxylic acid chloride. The product obtained was dissolved in 10 ml of toluene, and the solution was added dropwise to a solution of 1.04 g of 2-[2,6-dimethyl-4-(2-ethoxyethyl)-phenoxy]-ethylamine and 0.6 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.3 g of the title compound.

(10) Synthesis of N-(2-[2-methyl-4-(2-n-propoxyethyl)-phenoxy]ethyl)-2,6-dimethyl-cyclopenta[1,2-c]-3-pyrazolecarboxamide (Compound 20)

In 1.5 ml of thionyl chloride was refluxed 0.7 g of 2,6-dimethyl-cyclopenta[1,2-c]-3-pyrazolecarboxylic acid under heating for 3 hours.

After completion of the reaction, excessive thionyl chloride was removed under reduced pressure to obtain 2,6-dimethyl-cyclopenta[1,2-c]-3-pyrazolecarboxylic acid chloride. The product obtained was dissolved in 10 ml of toluene, and the solution was added dropwise to a solution of 1.04 g of 2-[2-methyl-4-(2-n-propoxyethyl)-phenoxy]-ethylamine and 0.6 g of triethylamine dissolved in 10 ml of toluene while ice cooling and stirring.

After completion of the dropwise addition, the mixture was stirred at room temperature for 1 hour to complete the reaction. Subsequently, water was added to the reaction mixture, and the mixture was extracted with toluene. The extract was washed with 1N-sodium hydroxide, and further washed with water. The resulting solution was dried over anhydrous sodium sulfate, and the solvent was removed under reduced pressure.

The residue obtained was purified by silica gel column chromatography (Wako gel C-200 (trade name, manufactured by Wako Junyaku K. K.), eluted by toluene:ethyl acetate=3:1) to obtain 1.1 g of the title compound.

Example 2 (Preparation of formulations)

(1) Preparation of granule 5 parts by weight of Compound 6 was uniformly mixed with 35 parts by weight of bentonite, 57 parts by weight of talc, 1 part by weight of Neopelex powder (trade name, produced by Kao K. K.) and 2 parts by weight of sodium lignosulfonate, and then, the mixture was kneaded with addition of a small amount of water, followed by granulation and drying, to obtain a granule.

(2) Preparation of wettable powder 10 parts by weight of Compound 6 was uniformly mixed with 67.5 parts by weight of kaolin, 20 parts by weight of white carbon, 2 parts by weight of Neopelex powder (trade name, produced by Kao K. K.) and 0.5 part by weight of Demol (trade name, produced by Kao K. K.), and then the mixture was pulverized to obtain a wettable powder.

(3) Preparation of emulsion 20 parts by weight of Compound 6 was uniformly mixed with 70 parts by weight of xylene by adding 10 parts by weight of Toxanone (trade name, produced by Sanyo Kasei Kogyo K. K.), and dissolved therein to obtain an emulsion.

(4) Preparation of dust 5 parts by weight of Compound 6 was uniformly mixed with 50 parts by weight of talc and 45 parts by weight of kaolin to obtain a dust.

Example 3 (Tests of effects)

(1) Test of effect on green rice leafhopper

The respective wettable powders of the compounds (I) shown in Tables 1 to 4 prepared as in Example 2 were diluted to 100 ppm with water containing a surfactant (0.01 %). In these respective chemicals obtained, young seedlings of rice were dipped for 15 seconds, respectively, air-dried and put into the respective glass cylinders.

Subsequently, 10 green rice leafhoppers (4th instar nymphs) were placed in the respective cylinders. The cylinders were closed with porous caps and left to stand in a thermostat chamber at 25° C. After 4 days, insecticidal rate was determined by counting living and dead insects.

The insecticidal effect was evaluated by using 4 ranks depending on the range of insecticidal rate (A: 100 %, B: 99 to 80 %, C: 79 to 60 % and D: 59 % or less).

These results are shown in Table 5.

TABLE 5

| Test of effect on green rice leafhopper | |
|---|---|
| Compound | Effect |
| 1 | A |
| 2 | A |
| 3 | A |
| 6 | B |
| 8 | A |
| 10 | A |
| 11 | A |
| 12 | A |
| 13 | A |
| 14 | A |
| 19 | A |
| 20 | A |

(2) Test of effect on two-spotted spider mite female adult

The respective wettable powders of the compounds (I) shown in Tables 1 to 4 prepared as in Example 2 were diluted to 300 ppm with water containing a surfactant (0.01%), and in these respective chemicals obtained, kidney bean leaves (diameter: 20 mm) on which 10 two-spotted spider mite female adults were parasitic were dipped for 15 seconds, respectively.

Subsequently, these respective leaves were left to stand in a thermostat chamber at 25° C., and after 3 days, acaricidal rate was determined by counting living and dead insects in the respective leaves.

The results of evaluation of the acaricidal effect are shown in Table 6 according to the 4 rank evaluation method described in the above (1).

TABLE 6

| Test of effect on two-spotted spider mite | |
|---|---|
| Compound | Effect |
| 1 | A |
| 2 | A |
| 3 | A |
| 4 | B |
| 5 | A |
| 7 | B |
| 8 | A |
| 10 | A |
| 11 | A |
| 12 | A |
| 13 | B |
| 14 | A |
| 19 | B |
| 20 | A |

(3) Test of effect on two-spotted spider mite egg

The respective wettable powders of the compounds (I) shown in Tables 1 to 4 prepared as in Example 2 were diluted to 300 ppm with water containing a surfactant (0.01%), and in these respective chemicals obtained, kidney bean leaves (diameter: 20 mm) on which 10 two-spotted spider mite female adults were parasitic were dipped for 15 seconds, respectively.

Subsequently, these respective leaves were left to stand in a thermostat chamber at 25° C., and after 7 days, egg killing rate was determined by counting unhatched eggs in the respective leaves.

The egg killing effect was evaluated by using 4 ranks depending on the range of egg killing rate (A: 100%, B: 99 to 80%, C: 79 to 60% and D: 59% or less).

These results are shown in Table 7.

TABLE 7

| Test of effect on two-spotted spider mite egg | |
|---|---|
| Compound | Effect |
| 1 | A |
| 2 | A |
| 3 | A |
| 4 | A |
| 5 | A |
| 7 | A |
| 8 | A |
| 10 | A |
| 11 | A |
| 12 | A |
| 13 | B |
| 14 | A |
| 19 | A |
| 20 | A |

(4) Test of effect on diamond-back moth

The respective wettable powders of the compounds (I) shown in Tables 1 to 4 prepared as in Example 2 were diluted to 300 ppm with water containing a surfactant (0.01 %). In these respective chemicals obtained, cabbage leaves (5×5 cm) were dipped for 15 seconds, respectively, put into the respective plastic cups and then air-dried.

Subsequently, 10 diamond-back moths (3rd instar larvae) were placed in the respective cups. The cups were closed with caps and left to stand in a thermostat chamber at 25° C. After 2 days, insecticidal rate was determined by counting living and dead insects in the respective cups.

The results of evaluation of the insecticidal effect are shown in Table 8 according to the 4 rank evaluation method described in the above (1).

TABLE 8

| Test of effect on diamond-back moth | |
|---|---|
| Compound | Effect |
| 1 | B |
| 2 | B |
| 3 | B |
| 8 | B |
| 10 | A |
| 11 | A |
| 12 | A |
| 13 | B |
| 14 | A |
| 19 | B |
| 20 | A |

(5) Test of effect on brown leafhopper

The respective wettable powders of the compounds (I) shown in Tables 1 to 4 prepared as in Example 2 were diluted to 300 ppm with water containing a surfactant (0.01 %). In these respective chemicals obtained, young seedlings of rice were dipped for 30 seconds, respectively, air-dried and put into the respective glass cylinders.

Subsequently, 10 brown leafhoppers (3rd instar larvae) were placed in the respective glass cylinders. The cylinders were closed with porous caps and left to stand in a thermostat chamber at 25° C. After 4 days, insecticidal rate was determined by counting living and dead insects in the respective glass cylinders.

The results of evaluation of the insecticidal effect are shown in Table 9 according to the 4 rank evaluation method described in the above (1).

TABLE 9

| Test of effect on brown leafhopper | |
|---|---|
| Compound | Effect |
| 1 | B |
| 10 | A |
| 11 | A |
| 12 | A |
| 14 | B |
| 19 | A |
| 20 | A |

(6) Test of controlling effect on powdery mildew (barley) (prevention effect)

In plastic flowerpots having a diameter of 6 cm, 10 barleys (variety: Kuromugi) were grown per one flowerpot, and to the young plants at 1.5 leaf stage, the chemicals obtained by diluting the wettable powders of the compounds (I) shown in Tables 1 to 4 prepared as in Example 2 to 500 ppm with water containing a surfactant (0.01%) were sprayed in an amount of 20 ml per one flowerpot, respectively.

These barleys were grown in a glass greenhouse for 2 days, and then conidiospores of powdery mildew (barley) collected from infected leaves were dusted uniformly over the respective plants to be inoculated thereinto.

Then, these plants were grown in a glass greenhouse for one week, and the degree of lesion of powdery mildew (barley) appeared on the respective first leaves was examined.

The fungicidal effect was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

These results are shown in Table 10.

TABLE 10

| Test of controlling effect on powdery mildew (barley) | |
|---|---|
| Compound | Effect |
| 2 | 4 |
| 3 | 5 |
| 5 | 5 |
| 8 | 5 |
| 11 | 5 |
| 12 | 5 |
| 13 | 4 |
| 14 | 4 |
| 17 | 4 |
| 18 | 4 |
| 20 | 4 |
| Non-treated district | 0 |

(7) Test of controlling effect on brown rust (wheat) (prevention effect)

In plastic flowerpots having a diameter of 6 cm, 10 wheats (variety: Kobushi wheat) were grown per one flowerpot, and to the young plants at 1.5 leaf stage, the chemicals obtained by diluting the wettable powders of the compounds (I) shown in Tables 1 to 4 prepared as in Example 2 to 500 ppm with water containing a surfactant (0.01%) were sprayed in an amount of 20 ml per one flowerpot, respectively. After spraying, the wheats were grown in a glass greenhouse for 2 days, and then a suspension of spores of brown rust (wheat) (2 to $3 \times 10^5$/ml) was sprayed uniformly to the plants to be inoculated thereinto.

After inoculation, the wheats were grown in a glass greenhouse for one week, and the degree of lesion of brown rust (wheat) appeared on the first leaves was examined.

The results are shown in Table 11 according to the 6 rank evaluation method described in the above (6).

TABLE 11

Test of controlling effect on brown rust (wheat)

| Compound | Effect |
|---|---|
| 2 | 5 |
| 3 | 4 |
| 5 | 4 |
| 8 | 5 |
| 10 | 5 |
| 11 | 4 |
| 20 | 4 |
| Non-treated district | 0 |

(8) Test of controlling effect on blast (rice) (prevention effect)

In plastic flowerpots having a diameter of 6 cm, 10 rices (variety: Nipponbare) were grown per one flowerpot, and to the young plants at 1.5 leaf stage, the chemicals obtained by diluting the wettable powders of the compounds (I) shown in Tables 1 to 4 prepared as in Example 2 to 500 ppm with water containing a surfactant (0.01%) were sprayed in an amount of 20 ml per one flowerpot, respectively.

After spraying, the rices were grown in a glass greenhouse for 2 days, and then a suspension of conidiospores of blast (rice) collected from infected leaves was sprayed uniformly to the plant leaves to be inoculated thereinto.

After inoculation, the rices were grown in a glass greenhouse at 28° C. for 5 days, and the degree of lesion of blast (rice) appeared on the leaves was examined.

The results are shown in Table 12 according to the 6 rank evaluation method described in the above (6).

TABLE 12

Test of controlling effect on blast (rice)

| Compound | Effect |
|---|---|
| 1 | 4 |
| 2 | 5 |
| 3 | 4 |
| 8 | 4 |
| 9 | 4 |
| 11 | 5 |
| 12 | 5 |
| 13 | 4 |
| 14 | 4 |
| 17 | 4 |
| Non-treated district | 0 |

The novel phenoxyalkylamine derivative of the present invention has an excellent effect of controlling noxious organisms such as insecticidal, acaricidal and fungicidal effects.

We claim:

1. A phenoxyalkylamine compound represented by the following formula:

(I)

[Chemical structure: bicyclic pyrazole-fused cyclopentane with N-N-$R^1$ group, connected via C=N to CONHCH$_2$CH$_2$O-phenyl with $R^3$, $R^4$, $R^5$ substituents; $R^2$ on the cyclopentane ring]

wherein $R^1$ represents a lower alkyl group; $R^2$ represents hydrogen atom or a lower alkyl group; $R^3$ represents hydrogen atom or a lower alkyl group; $R^4$ represents —A—O—$R^6$ where A represents a lower alkylene group and $R^6$ represents a lower alkyl group, a lower alkenyl group or a lower alkynyl group; and $R^5$ represents hydrogen atom or a lower alkyl group.

2. The compound according to claim 1, wherein $R^1$ is methyl group or 2,2,2-trifluoroethyl group.

3. The compound according to claim 1, wherein $R^2$ is hydrogen atom or methyl group.

4. The compound according to claim 1, wherein $R^3$ is methyl group.

5. The compound according to claim 1, wherein $R^4$ is allyl group, ethoxymethyl group, 2-methoxyethyl group, 2-ethoxyethyl group, 2-propoxyethyl group, 2-butoxyethyl group, 2-allyloxyethyl group or 2-propargyloxyethyl group.

6. The compound according to claim 1, wherein $R^5$ is hydrogen atom or methyl group.

7. The compound according to claim 1, wherein said compound is at least one selected from the group consisting of N-[2-(4-allyl-2-methylphenoxy)ethyl]-2-methyl-cyclopenta[1,2-c]-3pyrazolecarboxamide, N-{2-[4-(2-methoxyethyl)-2-methylphenoxy]ethyl}-2-methyl-cyclopenta[1,2-c]-3-pyrazolecarboxamide, N-{2-[4-(2-ethoxyethyl)-2-methyl-phenoxy]ethyl}-2-methyl-cyclopenta[1,2-c]-3-pyrazolecarboxamide, N-{2-[4-(2-n-propoxyethyl)-2-methylphenoxy]-ethyl}-(2-[4-(2-allyloxyethyl)-2-methylphenoxy]ethyl}-2-methyl-cyclopenta[1,2-c]-3-pyrazolecarboxamide, N-(2-[2,3-dimethyl-4-(2-ethoxyethyl)phenoxy]ethyl)-2-methyl-cyclo-penta[1,2-c]-3-pyrazolecarboxamide, N-(2-[4-(2-ethyl}-2-methoxyethyl)-2-methylphenoxy]ethyl)-2-methyl-cyclopenta-[1,2-c]-3-pyrazolecarboxamide, N-(2-[4-(2-methoxyethyl)-2-pyrazolecarboxamide, N-(2-[4-(2-ethoxyethyl)-2-methyl-phenoxy]ethyl)-2,6-dimethyl-cyclopenta[1,2-c]-3-pyrazole-carboxamide, N-(2-[4-(2-allyloxyethyl)-2-methylphenoxy]-ethyl)-2,6-dimethyl-cyclopenta[1,2-c]-3-pyrazolecarboxamide, N-{2-[4-(2-propargyloxyethyl)-2-methylphenoxy]-ethyl)-2,6-dimethyl-cyclopenta[1,2-c]-3-pyrazolecarboxamide, N-(2-[2,3-dimethyl-4-(2-ethoxyethyl)-phenoxy]ethyl}-2,6-dimethyl-cyclopenta[1,2-c]-3-pyazolecarboxamide, N-(2-[2,6-dimethyl-4-(2-ethoxyethyl)phenoxy]ethyl)-2,6-dimethyl-cyclopenta[1,2-c]-3-pyrazolecarboxamide and N-(2-[2-methyl-4-(2-n-propoxyethyl)phenoxy]ethyl)-2,6-dimethyl-cyclopenta-[1,2-c]-3-pyrazolecarboxamide.

8. A composition for controlling noxious organisms comprising the phenoxyalkylamine compound represented by the formula (I) according to claim 1 as an active ingredient and an insecticidally, acaricidally or fungicidally suitable carrier.

* * * * *